(12) United States Patent
Isaacson et al.

(10) Patent No.: US 6,190,327 B1
(45) Date of Patent: Feb. 20, 2001

(54) DISPOSABLE AIRWAY ADAPTER FOR USE WITH A CARBON DIOXIDE DETECTOR

(75) Inventors: Phillip O. Isaacson, Chanhassen; Timothy L. Johnson; William F. Kratoska, both of Plymouth; Kathlean Cain Zinnel, Bloomington, all of MN (US)

(73) Assignee: Nonin Medical, Inc., Plymouth, MN (US)

(*) Notice: Under 35 U.S.C. 154(b), the term of this patent shall be extended for 0 days.

(21) Appl. No.: 09/305,517

(22) Filed: May 5, 1999

(51) Int. Cl.[7] ........................................... A61B 5/08
(52) U.S. Cl. .................. 600/529; 600/532; 73/23.3; 250/339.13; 250/353; 356/437
(58) Field of Search ...................... 600/529, 532; 73/23.3; 250/339.13, 341.1, 343, 353; 356/437

(56) References Cited

U.S. PATENT DOCUMENTS

| | | | |
|---|---|---|---|
| 4,322,621 | * 3/1982 | Aagard | 250/343 |
| 4,549,553 | * 10/1985 | Hochberg | 600/532 |
| 4,914,720 | 4/1990 | Knodle et al. | 250/343 |
| 4,998,018 | * 3/1991 | Kurahashi et al. | 250/343 |
| 5,067,492 | * 11/1991 | Yelderman et al. | 600/532 |
| 5,095,913 | * 3/1992 | Yelderman et al. | 600/532 |
| 5,159,934 | 11/1992 | Hoberman | 600/532 |
| 5,282,473 | * 2/1994 | Braig et al. | 600/532 |
| 5,445,160 | 8/1995 | Culver et al. | 600/532 |
| 5,789,660 | * 8/1998 | Kofoed et al. | 73/23.2 |
| 5,957,127 | * 9/1999 | Yamamori et al. | 600/532 |
| 5,973,326 | * 10/1999 | Parry et al. | 250/343 |
| 6,044,843 | * 4/2000 | O'Neil et al. | 600/529 |

\* cited by examiner

*Primary Examiner*—Cary O'Connor
*Assistant Examiner*—Navin Natnithithadha
(74) *Attorney, Agent, or Firm*—Vidas, Arrett & Steinkraus, P.A.

(57) ABSTRACT

The invention is directed to a disposable airway adapter which includes two optical windows and a reflector, positioned such that radiation transmitted through the first optical window into the airway passage will be reflected by the reflector and be transmitted through the second optical window and out of the airway passage. the disposable airway adapter is for use in connection with a carbon dioxide detector for determining the concentration of carbon dioxide present in the mixture of gases present in the airway passage.

36 Claims, 4 Drawing Sheets

DISPOSABLE AIRWAY ADAPTER FOR USE WITH A CARBON DIOXIDE DETECTOR

CROSS-REFERENCE TO RELATED APPLICATIONS

Not applicable.

STATEMENT REGARDING FEDERALLY SPONSORED RESEARCH

Not applicable.

BACKGROUND OF THE INVENTION

This invention relates generally to a disposable airway adapter for use in connection with a carbon dioxide detector, and more particularly an airway adapter which includes two optical windows and a reflector, arranged relative to each other such that infrared radiation transmitted through the first optical window is reflected by the reflector and transmitted out through the second optical window.

One of the most important aspects of critical care is the clinician's management of the patient's airway. Oral intubation, or the placement of an endotracheal or airway tube in the trachea of a patient has become a routine procedure used to maintain a clear airway in most surgical, emergency, and intensive care situations. Failure to achieve tracheal intubation may result in the airway tube being placed in the esophagus and diverting air flow from the lungs may cause patient complications or death. One common way to determine proper endotracheal tube placement is to measure the exhaled carbon dioxide concentration of the patient through the airway tube. Carbon dioxide will normally be present in the exhalation, assuming proper placement, but in most situations will not be present in gases exiting from an esophageal tube.

Carbon dioxide detectors for this purpose are known in the art. For example, U.S. Pat. No. 4,914,720 appears to be directed to a device where an emitter and detector are arranged directly across from each other in an in-line relationship. U.S. Pat. No. 5,445,160 also is directed to a portable carbon dioxide monitor wherein the light source (emitter) is placed in a disposable airway adaptor. The entire contents of U.S. Pat. No. 4,914,720 and U.S. Pat. No. 5,445,160 are hereby incorporated by reference. U.S. Pat. No. 5,445,160 provides semi-quantitative measurements of carbon dioxide concentration. Capnometers are well known in the art and can provide more accurate measurements of carbon dioxide concentration than semi-quantitative devices by utilizing more than one wavelength of light.

The greater the distance the infrared radiation travels, the greater the absorption, which results in a more accurate measurement of the concentration of the designated gas, especially at low concentrations of the designated gas. However, the prior art arrangement of the emitter and detector being in an in-line relationship does not maximize the distance the infrared radiation can travel, and therefore does not provide the best results.

A need therefore exists for a monitoring device for measuring and indicating the concentration of exhaled carbon dioxide which is durable, storable, portable, easy to use, sensitive, reliable, safe, inexpensive, clean, and disposable.

BRIEF SUMMARY OF THE INVENTION

The present invention meets the needs described above by providing a disposable airway adapter for use in connection with a carbon dioxide detector which includes two optical windows and a reflector, arranged relative to each other such that infrared radiation transmitted through the first optical window is reflected by the reflector and transmitted out through the second optical window.

The carbon dioxide detector includes a sensor module with an emitter and an infrared detector arranged to snap-fit around the disposable airway adapter. The emitter transmits infrared light through the first optical window, which is reflected off of the reflector and is then transmitted out the second optical window, through an optical filter to the infrared detector.

The adapter tube, optical windows and reflector are made of clear biocompatible plastic material. The reflector is plated with aluminum to provide a reflective surface. The surfaces of the windows and the reflector are coated with an anti-fog coating to minimize fogging due to moisture level changes in the respiration cycle.

The optical filter is most transmissive at 4.26 micrometers, which is the wavelength at which carbon dioxide is most absorptive.

The angular path of the infrared radiation between the emitter, reflector and detector defines an angle of less than 90°, and in the preferred embodiment is approximately 46°.

These and other advantages and features which characterize the invention are pointed out with particularity in the claims annexed hereto and forming a further part hereof. However, for a better understanding of the invention, its advantages and objects obtained by its use, reference should be made to the drawings which form a further part hereof, and the accompanying descriptive matter, in which there is illustrated and described a preferred embodiment of the invention.

BRIEF DESCRIPTION OF THE DRAWINGS

In the drawings, wherein like reference numerals represent like parts throughout the several views.

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

Figure 1:
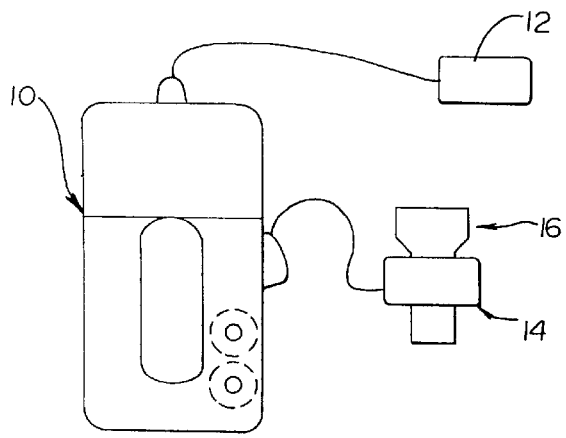
FIG. 1 is a schematic view of a combined pulse oximeter/carbon dioxide detector ($SPO_2/CO_2$) according to the present invention.
Figure 2:
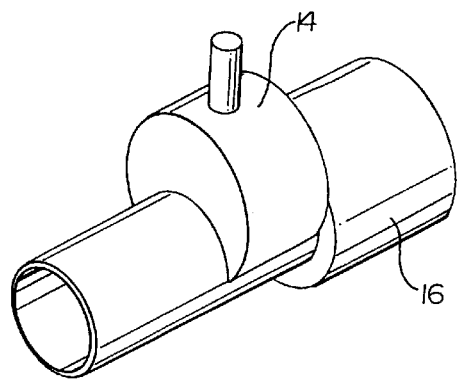
FIG. 2 is a perspective view of the disposable airway adapter of the present invention attached to the sensor module of the $CO_2$ detector.

Referring now to FIGS. 1 and 2, a combination pulse oximeter/carbon dioxide ($SPO_2/CO_2$) detector is shown at 10, with an oximeter sensor 12 shown conductively connected to the detector 10, a carbon dioxide sensor module 14 shown conductively connected to the detector 10 and the sensor module 14 shown connected to a disposable airway adapter tube 16. Although the present invention is disclosed in connection with a combination ($SPO_2/CO_2$) detector it should be understood that the disposable airway adapter tube 16, discussed more fully below, could be used in connection with a stand-alone carbon dioxide detector, which are well known in the art. The technology related to infrared absorption spectroscopy, for measuring carbon dioxide, is a well known and defined art.

The pulse oximeter portion of the device could be any commercially available pulse oximeter, although in the preferred embodiment it is based on the pulse oximeter technology of applicant, including the Model 8600 Portable Pulse Oximeter and the Model 8500 Hand Held Pulse Oximeter. Applicant owns several patents related to this technology, including U.S. Pat. No. 4,773,422; U.S. Pat. No. RE 33,643, and U.S. Pat. No. 5,490,523, and the entire contents of these patents are hereby incorporated by reference.

The detector 10 is intended to provide semi-quantitative $CO_2$ values for intubated patients. The present invention can be used in any situation where a visible and audible indication of patient respiration and intubation verification are needed, although its design makes it particularly suitable for patient transport situation such as ambulances and emergency rooms. It should also be understood that any commonly available semi-quantitative carbon dioxide detector, as well as any commercially available capnometer could be easily adapted to work with the inventive disposable airway adapter.

Figure 3:
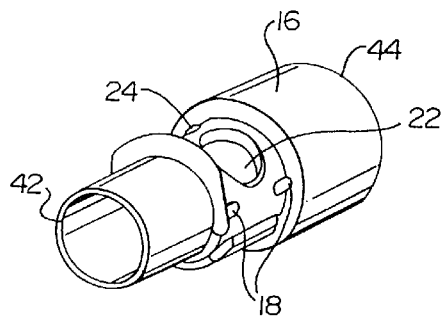
FIG. 3 is a more detailed perspective view of the disposable airway adapter of the present invention.

Referring now to FIG. 3, the adapter 16 is preferably made of a clear molded biocompatible plastic material such as polycarbonate. Detents 18 are provided on both sides of adapter 16 to allow the adapter 16 to snap-fit with the sensor module 14. As can be seen best in FIG. 4, detents 18 snap-fit into depressions 20 to securely hold the adapter 16 to sensor module 14. Optical windows 22 and 24 are provided in adapter 16. As can be seen best in connection with FIG. 5, optical windows 22 and 24 are made of a continuous piece of clear biocompatible plastic material 26 which is bonded to the outside of adapter 16, for example Mylar. Reflector 28 is also bonded to adapter 16 and is made of a clear molded biocompatible plastic material. Raised flat portion 30 is coated with a highly reflective coating of aluminum.

Figure 4:
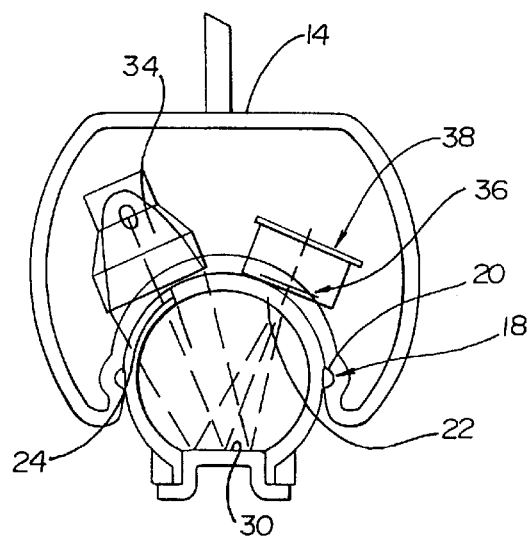
FIG. 4 is a cross sectional schematic view of the sensor module and disposable airway adapter tube.
Figure 5:
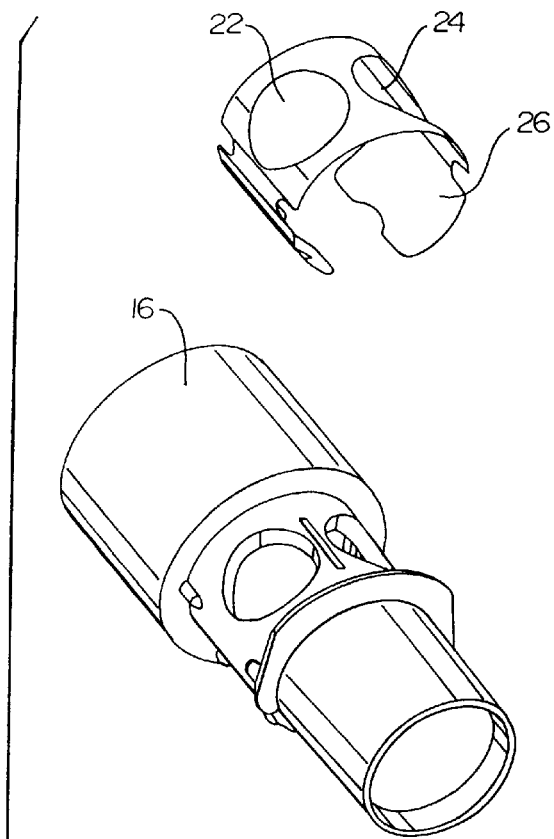
FIG. 5 is an exploded view of the disposable airway adapter.
Figure 6:
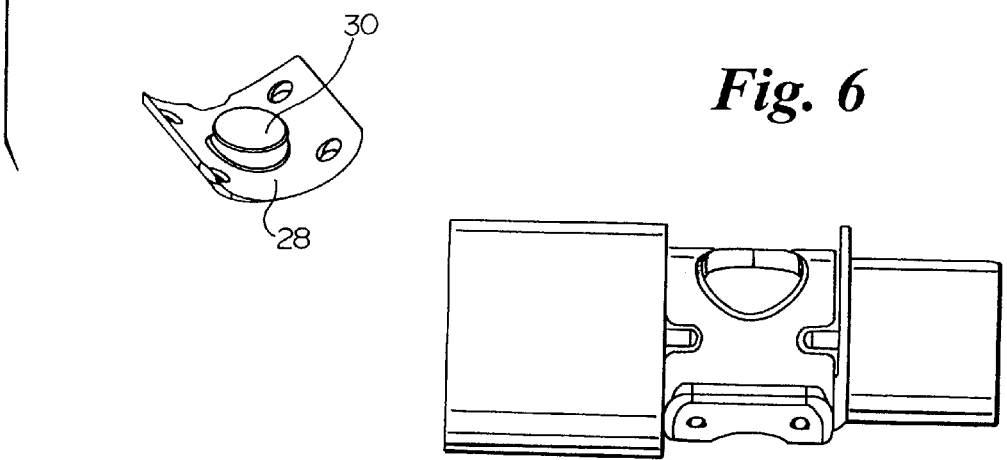
FIG. 6 is a perspective view of the disposable airway adapter.
Figure 7:
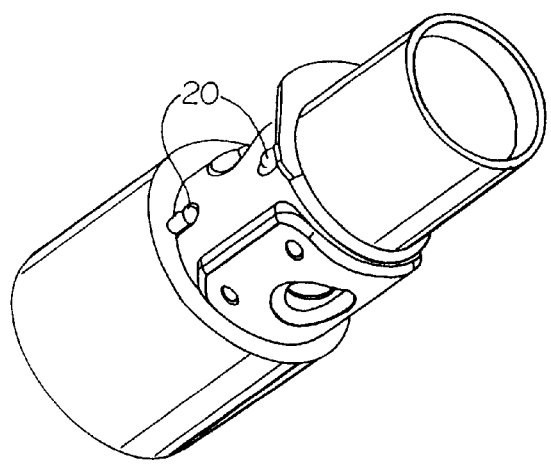
FIG. 7 is a perspective view of the disposable airway adapter.

Referring now to FIG. 4, in operation tungsten filament lamp emitter 34 emits infrared radiation which is transmitted through optical window 24. The radiation continues through the gases present in adapter tube 16, strikes the flat reflective surface 30 of reflector 28 and the radiation is transmitted out through optical window 22, through optical filter 36 and to infrared detector 38. Optical filter 36 is most transmissive at 4.26 micrometers, which is where carbon dioxide is most absorptive. Emitter 34, filter 36 and sensor 38 are well known components to those of ordinary skill in the art. In the preferred embodiment the angular path of the infrared radiation between the emitter 34, reflector 28 and detector 38 defines an angle of less than 90°, and most preferably about 46°.

In the preferred embodiment, emitter 34 is a tungsten filament lamp. The preferred emitter consists of a two-lead tungsten-filament bulb permanently mounted in an elliptical reflector. An appropriate emitter element will have a low-cost tungsten filament, T-1 size, optionally with a well-centered filament, an elliptical reflector of chrome-plated plastic and a sapphire bulb protector window. The emitter will have a modulation frequency of 6.25 Hz, a rectangular modulation wave shape, approximately 50% duty cycle. The filament bulb characteristics will affect emitter current. The circuit voltage will be 5.0 V and the series resistance approximately 22 ohms.

In the preferred embodiment, detector 38 is a pyroelectric IR sensor element combined with a narrow band optical filter. The filter is most transmissive at approximately 4.26 m, the wavelength at which $CO_2$ is most absorptive. The most preferred optical filter has a center wavelength of 4.26 micrometers and a half-power bandwidth of 0.18 micrometers. A typical device meeting these requirements is the Heimann LHi-807-TC-G2. Detector 38 may be a commercially available device, removably mounted in the sensor housing, which is pyroelectric, has a temperature compensated dual-element with integral FET source follower, in TO-5 housing with an integral optical filter 36.

Figure 8:
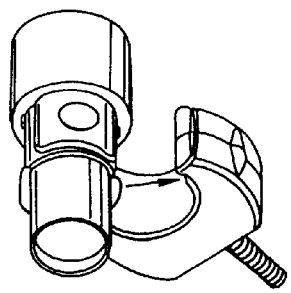
FIG. 8 shows the disposable airway adapter partially inserted into the sensor module.
Figure 9:
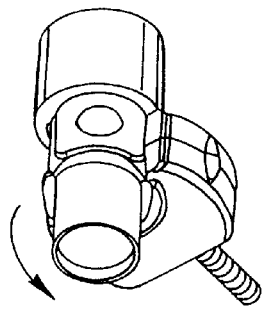
FIG. 9 shows the disposable airway rotating into the sensor module.
Figure 10:
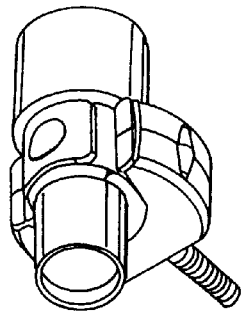
FIG. 10 shows the disposable airway fully inserted into the sensor module.

The attachment method for connecting adapter 16 to sensor module 14 is shown in FIGS. 8–10. One of detents 18 is placed into its corresponding depression 20 and the adapter 16 is rotated into sensor module until the other detents 18 snap-fit into their respective depressions 20.

The airway adapter 16 is recommended for one-time use, and is compatible with established intubation methods and equipment. Adapter 16 is symmetric with respect to a plane through its center, and can be snapped onto sensor module 14 in either direction. The overall length of adapter 16 is approximately 55 mm, with an outer diameter of 15 mm at first end 42 and 15 mm inner diameter, 22 mm outer diameter at second end 44.

Figure 11:
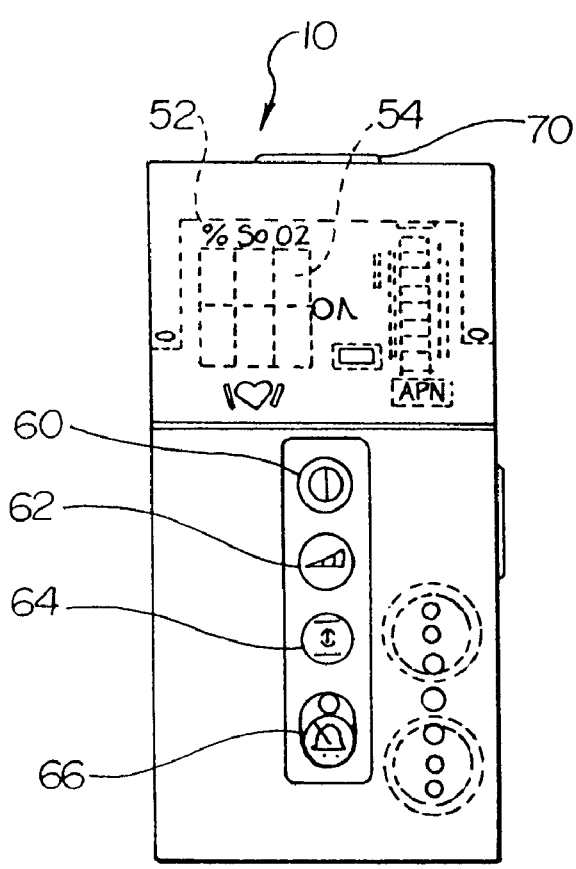
FIG. 11 shows a top view of the controls of the $SPO_2/CO_2$ detector.
Figure 12:
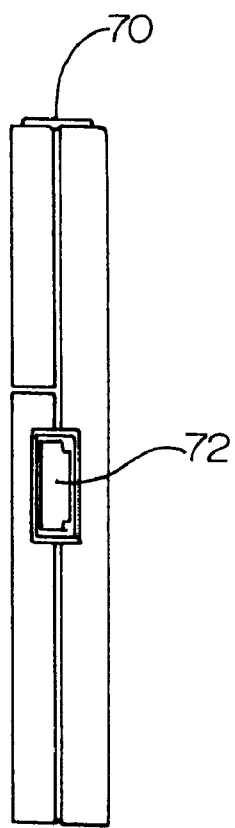
FIG. 12 shows a side view of the $SPO_2/CO_2$ detector.

Referring now to FIGS. 11 and 12, combined $SpO_2/CO_2$ detector 10 is shown in more detail. Detector 10 includes control panel 50 and display board 52, which includes blood oxygen and heart rate display 54, and $CO_2$ level indicator 56. In a preferred embodiment as shown, casing 28 of detector 10 is approximately 3"×6"×1". $CO_2$ level indicator 52 may be a "semi-quantitative" indicator, or bar graph display as shown in FIG. 11. Control panel 50 includes a four-button membrane switch keypad, which include an on/off switch 60, an advance switch 62, an alarm limit switch 64 and an audible alarm disable switch 66. The pulse oximeter cable connector is shown at 70 and the carbon dioxide cable connector is shown at 72.

Detector 10 may optionally have a memory component and audible indicator means (not shown). When equipped with the memory option, up to 18 hours of blood oxygen, heart rate, and respiration rate information may be stored. Data storage and retrieval are implemented as set forth in U.S. Pat. No. 5,490,523.

Monitor 10 has the capability of sending the current $SpO_2$, heart rate, $CO_2$ measurement, and respiration rate data to the 9-pin sub-D connector in an 8-bit no parity format once per second in the real-time mode. This information may then be printed, collected or displayed as required.

The system is safe, rugged, easy to use and easy to clean by health care professionals. No warm-up time is required. The system is fully operational after a several second power-on initialization sequence, provided the sensors or monitor are not transitioning from a non-operating environment, and remains fully operational with a reasonable level of water vapor or patient secretions in the patient airway adapter and/or on the sensor module or monitor itself.

It should be understood that the adapter structure 16 disclosed could be used to identify any designated gas with suitable emitters, detectors and filters, and is not intended to be limited to carbon dioxide. It should also be understood that although the invention is disclosed in a combination pulse oximeter and carbon dioxide detector, the inventive adapter 16 could be used in connection with a standalone carbon dioxide detector or capnometer.

The above examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A disposable airway adapter tube comprising:
   an adapter tube body defining an airway passage, the adapter tube body including first and second optical windows;
   a reflector positioned in the airway passage;
   the first and second optical windows being positioned relative to the reflector such that radiation transmitted through the first optical window into the airway passage will be reflected by the reflector and be transmitted through the second optical window and out of the airway passage.

2. The disposable airway adapter tube of claim 1, further in combination with a carbon dioxide detector.

3. The disposable airway adapter tube of claim 2, wherein the carbon dioxide detector is a semi-quantitative device.

4. The disposable airway adapter tube of claim 2, wherein the carbon dioxide detector is a capnometer.

5. The disposable airway adapter tube of claim 1, further in combination with a carbon dioxide detector/pulse oximeter device.

6. The disposable airway adapter tube of claim 2 wherein the radiation transmitted through the first window and out the second window is used to determine the concentration of a designated gas present in the airway passage.

7. The disposable airway adapter tube of claim 6 wherein the measured radiation is at a single wavelength.

8. The disposable airway adapter tube of claim 6 wherein the measured radiation is at two or more wavelengths.

9. The disposable airway adapter tube of claim 1 wherein the adapter tube body is made of a clear molded biocompatible plastic material.

10. The disposable airway adapter tube of claim 1 wherein the first and second optical windows are made of a clear biocompatible plastic material.

11. The disposable airway adapter tube of claim 10 wherein the airway passage is cylindrical and an inside surface of the first and second optical windows is coated with an anti-fog coating.

12. The disposable airway adapter tube of claim 1 wherein the reflector is made of a clear molded biocompatible plastic material and plated with a reflective material.

13. The disposable airway adapter tube of claim 12 wherein the reflective material is an aluminum coating.

14. The disposable airway adapter tube of claim 13 wherein the reflective material is coated with an anti-fog coating.

15. The disposable airway adapter tube of claim 1 wherein the radiation transmitted through the first window and out the second window is used to determine the concentration of a designated gas present in the airway passage.

16. The disposable airway adapter tube of claim 15 wherein the radiation is infrared.

17. The disposable airway adapter tube of claim 16 wherein the designated gas is carbon dioxide.

18. The disposable airway adapter tube of claim 2 wherein the adapter tube body is connected to the carbon dioxide detector, the carbon dioxide detector comprising:
   an emitter for transmitting infrared radiation into the airway passage through the first optical window;
   an infrared detector for detecting infrared radiation transmitted out of the airway passage through the second optical window;
   the carbon dioxide detector including circuitry for determining the amount of infrared radiation absorbed by the carbon dioxide present in a mixture of gases in the airway passage, which is proportional to the carbon dioxide concentration in the mixture of gases.

19. The disposable airway adapter tube of claim 18 further including an optical filter positioned between the infrared detector and the second optical window, the optical filter being most transmissive at a predetermined wavelength.

20. The disposable airway adapter tube of claim 19 in which the optical filter is most transmissive at approximately 4.26 micrometers.

21. The disposable airway adapter tube of claim 18 wherein the angular path of the infrared radiation between the emitter, reflector and detector defines an angle of less than 90°.

22. The combination of claim 21 wherein the angular path of the infrared radiation between the emitter, reflector and detector defines an angle of approximately 46°.

23. In combination, a gas detector and a disposable airway adapter tube, the gas detector for determining the concentration of a predetermined gas in a mixture of gases in the airway adapter tube, comprising:
   a gas detector including a sensor module;
   a disposable airway adapter tube body defining an airway passage, the disposable airway adapter tube body being removably connected to the sensor module, the disposable adapter tube body further including first and second optical windows;
   a reflector positioned in the airway passage;
   the sensor module including an emitter positioned for transmitting infrared radiation into the airway passage through the first optical window and an infrared detector positioned for detecting infrared radiation transmitted out of the airway passage through the second optical window;
   gas concentration circuitry for determining the amount of infrared radiation absorbed by the predetermined gas in the mixture of gases in the airway passage, which is proportional to the gas concentration in the mixture of gases.

24. The combination of claim 23 wherein the predetermined gas is carbon dioxide.

25. The combination of claim 24 further including an optical filter positioned between the infrared detector and the second optical window, the optical filter being most transmissive at a predetermined wavelength.

26. The combination of claim 25 in which the optical filter is most transmissive at approximately 4.26 micrometers.

27. The combination of claim 23 wherein the adapter tube body is made of a clear molded biocompatible plastic material.

28. The combination of claim 23 wherein the first and second optical windows are made of a clear biocompatible plastic material.

29. The combination of claim 28 wherein the airway passage is cylindrical and an inside surface of the first and second optical windows is coated with an anti-fog coating.

30. The combination of claim 29 wherein the reflector is made of a clear molded biocompatible plastic material and plated with a reflective material.

31. The combination of claim 30 wherein the reflective material is an aluminum coating.

32. The combination of claim 31 wherein the reflective material is coated with an anti-fog coating.

33. The combination of claim 23 wherein the sensor module and the disposable airway adaptor are constructed and arranged to snap-fit.

34. The combination of claim 23 wherein the angular path of the infrared radiation between the emitter, reflector and detector defines an angle of less than 90°.

35. The combination of claim 34 wherein the angular path of the infrared radiation between the emitter, reflector and detector defines an angle of approximately 46°.

36. A method of measuring a concentration of a designated gas present in a mixture of gases, the method comprising the following steps:
a) connecting a disposable airway adapter to a gas source, the airway adapter defining an airway passage and the airway adapter including first and second optical windows and a reflector positioned in the airway passage, the first and second optical windows being positioned relative to the reflector such that radiation transmitted through the first optical window into the airway passage will be reflected by the reflector and be transmitted through the second optical window and out of the airway passage;
b) transmitting infrared radiation through the first optical window so that it reflects off of the reflector and is transmitted out the second optical window;
c) determining the amount of infrared radiation absorbed by the designated gas in the mixture of gases in the airway passage, which is proportional to the gas concentration in the mixture of gases.

* * * * *